United States Patent [19]

Zinnen et al.

[11] Patent Number: 4,714,783

[45] Date of Patent: Dec. 22, 1987

[54] SEPARATION OF NITROBENZALDEHYDE ISOMERS

[75] Inventors: Hermann A. Zinnen, Evanston; Thad S. Franczyk, Skokie, both of Ill.

[73] Assignee: UOP Inc., Des Plaines, Ill.

[21] Appl. No.: 861,792

[22] Filed: May 12, 1986

[51] Int. Cl.[4] ............................................. C07C 76/06
[52] U.S. Cl. ..................................... 568/424; 568/438
[58] Field of Search ................................ 568/424, 438

[56] References Cited

U.S. PATENT DOCUMENTS

| | | | |
|---|---|---|---|
| 2,985,589 | 5/1961 | Broughton et al. | 210/660 |
| 3,706,812 | 12/1972 | Derosset et al. | 210/660 |
| 4,310,440 | 1/1982 | Wilson et al. | 252/435 |
| 4,402,832 | 9/1983 | Gerhold | 210/659 |
| 4,450,297 | 5/1984 | Preiss et al. | 568/424 |

OTHER PUBLICATIONS

Davey and Gwilt, J. Chem. Soc. 1950, 208.
"Continuous Adsorptive Processing—A New Separation Technique" by D. B. Broughton presented at the 34th Annual Meeting of the Society of Chemical Engineers at Tokyo, Japan on Apr. 2, 1969.
Abstract of Mourey et al., Anal. Chem., 51(6), 763-7 (1979).
Abstract of Pastuska et al., Chemiker Ztg. 88(9), 311-14 (1964).

*Primary Examiner*—Werren B. Lone
*Assistant Examiner*—Vera C. Clarke
*Attorney, Agent, or Firm*—Thomas K. McBride; John F. Spears, Jr.; Jack H. Hall

[57] ABSTRACT

A process for separating ortho- or meta-nitrobenzaldehyde from a feed mixture comprising ortho-nitrobenzaldehyde or metal-nitrobenzaldehyde and at least one other isomer from which the ortho- or metal-isomer is to be separated. The feed mixture is contacted at adsorption conditions with meta-selective adsorbent comprising a type X zeolite having sodium or lithium cations at exchangeable cationic sites or with an ortho-selective adsorbent comprising a type Y zeolite having alkali metal or alkaline earth metal cations at exchangeable cationic sites or a phosphate-substituted crystalline, aluminum silicate zeolite. Preferred desorbents are lower alkyl acetates and formates, acetonitrile and benzaldehyde.

20 Claims, 13 Drawing Figures

SEPARATION OF NITROBENZALDEHYDE ISOMERS

BACKGROUND OF THE INVENTION

The field of art to which the present invention relates is the separation of chemical isomers and more specifically, separation of the isomers of nitrobenzaldehydes through the employment of a bed of adsorbent.

BACKGROUND INFORMATION

There are several ways known for separating a mixture of the isomers of nitrobenzaldehyde. However, because the decomposition temperature is so near the distillation temperature (b.p.), for safety reasons, this method is ruled out; the high boiling points make separation by distillation energy intensive. Fractional crystallization is not satisfactory because the melting points are very close (ortho: 42°-44° C.; meta: 58° C.). Therefore, indirect methods are used, e.g., conversion of the isomers to acetals, which can be separated by distillation, as disclosed in U.S. Pat. No. 4,450,297, and then converted back to the nitrobenzaldehyde. A method of separating the isomers directly and avoiding costly chemical conversions and reconversion is still desired.

The known methods of making nitrobenzaldehydes result in mixtures of the isomers. For example, mixtures of ortho-nitrobenzaldehyde and meta-nitrobenzaldehyde prepared by the method of Davey and Gwilt, J. Chem. Soc. 1950, 208, results in a mixture of the following: up to 80% ortho-nitrobenzaldehyde; up to 20% meta-nitrobenzaldehyde and a small amount of para-nitrobenzaldehyde.

The present invention is based on the discovery that certain zeolites will effect a separation of isomeric nitrobenzaldehydes from each other by preferentially adsorbing one of the isomers. Recovery of one of the isomers thereof is effected by desorbing the selectively adsorbed isomer with particular desorbing agents.

SUMMARY OF THE INVENTION

In brief summary the present invention is, in one embodiment, a process for separating meta-nitrobenzaldehyde from a feed mixture comprising meta-nitrobenzaldehyde and at least one other isomer of nitrobenzaldehyde. The process comprises contacting the mixture at adsorption conditions with an adsorbent comprising an X-type zeolite having sodium or lithium cations at exchangeable cationic sites. The meta-isomer is selectively adsorbed to the substantial exclusion of the para and ortho-isomers, and para- and ortho-nitrobenzaldehyde are recovered in the raffinate stream.

In a second embodiment, the present invention is a process for separating ortho-nitrobenzaldehyde from a feed mixture comprising ortho-nitrobenzaldehyde and at least one other isomer of nitrobenzaldehyde. The process comprises contacting the mixture at adsorption conditions with an adsorbent comprisng a Y-type zeolite having alkali metal or alkaline earth metal cations at exchangeable cationic sites or a phosphate substituted crystalline alumina-silicate zeolite, selectively adsorbing the ortho-isomer to the substantial exclusion of the remaining isomers, removing the remaining isomers from contact with the adsorbent, and thereafter recovering high purity ortho-nitrobenzaldehyde.

DESCRIPTION OF THE INVENTION

The following definitions of various terms used throughout this specification will be used in describing the operation, objects and advantages of the present invention.

A "feed mixture" is a mixture containing one or more extract components and one or more raffinate components to be fed to an adsorbent of the process. The term "feed stream" indicates a stream of feed mixture which passes to an adsorbent used in the process.

An "extract component" is a type of compound or a compound, such as a particular isomer, that is more selectively adsorbed by the adsorbent while a "raffinate component" is a compound or type of compound that is less selectively adsorbed. In this process, the ortho-or e meta-isomers are extract components and the meta- and para-isomer or ortho- and para-isomers are raffinate components. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely non-adsorbed by the adsorbent. Therefore, small amounts of a raffinate component can appear in the extract stream, and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, in one embodiment, the ratio of concentration of the more selectively adsorbed meta-isomer to the concentration of less selectively adsorbed ortho- and para-isomers will be highest in the extract stream, next highest in the feed mixture, and lowest in the raffinate stream. Likewise, the ratio of the less selectively adsorbed ortho- and para-isomers to the more selectively adsorbed meta-isomer will be highest in the raffinate stream, next highest in the feed mixture, and the lowest in the extract stream. In the other embodiment referred to above, the ratio of concentration of the more selectively adsorbed ortho-isomer to the concentration of the less selectively adsorbed meta- and para-isomers will be highest in the extract stream, next highest in the feed stream and lowest in the raffinate stream. Likewise, the ratio of the less selectively adsorbed meta- and para-isomers to the more selectively adsorbed ortho-isomer will be highest in the raffinate stream, next highest in the feed mixture and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of the desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "non-selective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into the process for efficient operations to take place for a given quantity of adsorbent.

Feed mixtures which can be utilized in the process of this invention will comprise at least two nitrobenzaldehyde isomers. Isomers can be characterized by reference to Formula 1 below.

Formula 1

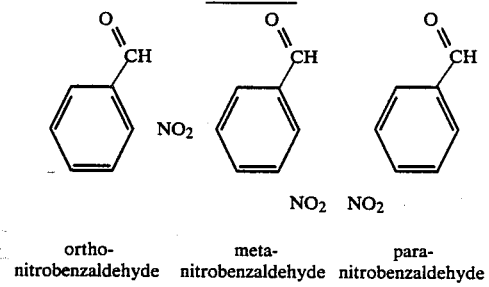

ortho-nitrobenzaldehyde    meta-nitrobenzaldehyde    para-nitrobenzaldehyde

The major use for ortho-nitrobenzaldehyde is in the manufacture of coronary dilating pharmaceuticals. The major outlets for meta-nitrobenzaldehyde are in the manufacture of pharmaceuticals, dyes, surface active agents, chlorophyll, antioxidant and mosquito repellant.

To separate a first nitrobenzaldehyde isomer from a feed mixture containing that isomer and at least one other nitrobenzaldehyde isomer, the mixture is contacted with the adsorbent and the first isomer is more selectively adsorbed and retained by the adsorbent, while the other isomers are relatively unadsorbed, with the first isomer being recovered as part of the extract stream, the other isomers, being relatively unadsorbed, would be recovered as part of the raffinate stream. In the present invention, either the ortho- or meta-isomer can be recovered as the extract product, depending on the choice of adsorbent. The adsorbed isomer is recovered from the adsorbent by contacting the adsorbent with a desorbent material. The term "desorbent material" as used herein shall mean any fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated continuously at substantially constant pressures and temperatures to ensure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, the desorbent must not react with either the adsorbent or any component of the feed material and must not reduce or destroy the critical selectivity of the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is, therefore, contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

In the preferred isothermal, isobaric, liquid-phase operation of the process of this invention, lower alkyl acetates, e.g., methyl acetate, ethyl acetate, propyl acetate and butyl acetate, lower alkyl formates, e.g., methylformate, ethylformate, acetonitrile and benzaldehyde have been found to be effective desorbents. The desorbent may be dissolved in a suitable diluent, such as toluene, so as to modify the rate of desorption as desired.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Equation 1
$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases, respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinite component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally, desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material with the desorbent material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and, therefore, permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a non-adsorbed tracer (n-octadecane for instance) and of the particular nitrobenzaldehyde isomers all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately by gas chromatography.

From information derived from the chromatographic traces, adsorbent performance can be rated in terms of capacity index for an extract component, selectivity for one isomer with respect to the other, and the rate of desorption of an extract component by the desorbent. The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The adsorbent to be used in the process of this invention comprises specific crystalline aluminosilicates. Crystalline aluminosilicates such as that encompassed by the present invention include crystalline aluminosilicate cage structures in which the alumina and silica tetrahedra are intimately connected in an open three-dimensional network. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves," although widely used, is not strictly suitable since the separation of specific aromatic isomers is apparently dependent on differences in electrochemical attraction of the different isomers and the adsorbent rather than solely on physical size differences in the isomer molecules.

In hydrated form, the crystalline aluminosilicates generally encompass those zeolites represented by the Formula below:

Formula 2

$M_{2/n}O:Al_2O_3:wSiO_2:yH_2O$ where "M" is a cation which balances the electrovalence of the tetrahedra and is generally referred to as an exchangeable cationic site, "n" represents the valence of the cation, "w" represents the moles of $SiO_2$, and "y" represents the moles of water. The generalized cation "M" may be monovalent, divalent or trivalent cations or mixtures thereof.

The prior art has generally recognized that adsorbents comprising the type X and the type Y zeolites can be used in certain adsorptive separation processes. These zeolites are well known to the art.

The type X structured zeolite in the hydrated or partially hydrated form can be represented in terms of mole oxides as shown in Formula 3 below:

Formula 3

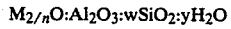
$(0.9\pm0.2)M_{2/n}O:Al_2O_3:(2.5\pm0.5)SiO_2:yH_2O$ where "M" represents at least one cation having a valence of not more than 3, "n" represents the valence of "M", and "y" is a value up to about 9 depending upon the identity of "M" and the degree of hydration of the crystal. As noted from Formula 3, the $SiO_2/Al_2O_3$ mole ratio is $2.5\pm0.5$. The cation "M" may be one or more of a number of cations such as the hydrogen cation, the alkali metal cation, or the alkaline earth cations, or other selected cations, and is generally referred to as an exchangeable cationic site. As the type X zeolite is initially prepared, the cation "M" is usually predominately sodium and the zeolite is, therefore, referred to as a sodium-type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in Formula 4 below:

Formula 4

$(0.9\pm0.2)M_{2/n}O:Al_2O_3\ _3:wSiO_2:yH_2O$ where "M" is at least one cation having a valence not more than 3, "n" represents the valence of "M", "w" is a value greater than about 3 up to 6, and "y" is a value up to about 9 depending upon the identity of "M", and the degree of hydration of the crystal. The $SiO_2/Al_2O_3$ mole ratio for type Y structured zeolites can thus be from about 3 to about 6. Like the type X structured zeolite, the cation "M" may be one or more of a variety of cations but, as the type Y zeolite is initially prepared, the cation "M" is also usually predominately sodium.

Another microporous crystalline material with which the invention can be practiced is the family of aluminophosphate composition synthesized by hydrothermal crystallization of an aluminophosphate gel containing a molecular structure-forming template, followed by calcination to yield a microporous crystalline adsorbent with uniform pores. The template can be an organic amine or a quaternary ammonium salt. These may be prepared by the procedure described in U.S. Pat. No. 4,310,440, which is incorporated herein by reference. Although others may be useful in the invention, particularly preferred is $AlPO_4$-5, which can be prepared as set forth in Examples 1-26 of said patent having a uniform pore size of 8 Å.

The principal characteristics of the $AlPO_4$-5 adsorbent used herein is specified as follows:

Chemical Analysis (wt. % anhydrous)
$Al_2O_3$—41.7
$P_2O_5$—57.8
Molar Ratio $P_2O_5/Al_2O_3$=1.00
Surface Area (1 pt. BET, $N_2$)—365m$^2$/g
$O_2$ Capacity ($-183_0$ C, 100 Torr)—14.1 %
Mean Particle Size (Coulter Counter)—4.9 micron The present invention is based on the discovery that the type Y zeolite with alkali metal or alkaline earth metal cations at exchangeable cation sites is more selective for the ortho-isomers of nitrobenzaldehye than for the meta- and para-isomers, and that the type X zeolite having alkali metal cations at exchangeable cationic sites, and preferably, sodium or lithium is more selective for the meta-isomer than the other isomers.

Typically, adsorbents used in separative processes contain the crystalline material dispersed in an amorphous binder material or inorganic matrix, having channels and cavities therein which enable liquid access to the crystalline material. Silica, alumina, or mixtures thereof are typical of such inorganic matrix materials. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh). Lower water content in the adsorbent is advantageous from the standpoint of having less water contamination of the product.

The adsorbent may be employed in the form of a dense fixed bed which is alternately contacted with a feed mixture and a desorbent material in which case the process will be only semicontinuous. In another embodiment, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in a static bed fluid-solid contacting may be used.

Moving bed or simulated moving bed flow systems, however, have a much greater separation efficiency than fixed bed systems and are, therefore, preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference for further explanation of the simulated moving bed countercurrent process flowscheme.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically, the concentration of desorbent material in the extract product and the raffinate product will be less than about 5 vol.% and more preferably less than about 1 vol.%. The separation means will typically be a fractionation column, the design and operation of which is well known to the separation art.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vaporphase operation. Adsorption conditions will include a temperature range of from about 20° C. to about 250° C. with about 100° C. to about 200° C. being more preferred and a pressure sufficient to maintain liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

The following examples are presented for illustration purposes and more specifically are presented to illustrate the selectivity relationships that make the process of the invention possible. Reference to specific cations, desorbent materials, feed mixtures and operating conditions is not intended to unduly restrict the scope and spirit of the claims attached hereto.

EXAMPLE I

In this experiment, the pulse test was performed to evaluate the ability of the present invention to separate isomers of nitrobenzaldehyde. The adsorbent used was a sodium-exchanged X zeolite and was mixed with 15 wt. % clay. Water was added and the resulting mixture was extruded, calcined at about 400° C., then ground to 20–60 mesh size. The adsorbent was re-dried at 350° C. before it was utilized in the process in each test. The desorbent used was methyl acetate.

The testing apparatus was the above-described pulse test apparatus. For each pulse test, the column was maintained at a temperature of 110° C. and a pressure of 125 psig to maintain liquid-phase operations. Gas chromatographic analysis equipment was used to analyze the column effluent stream in order to determine the composition of the effluent material at given time intervals. The feed mixture employed for each test comprised 2 cc pulses of a mixture containing about 0.5 g each of the three isomers, o-, m- and p-nitrobenzaldehyde, 0.25 g n-octadecane which was used as a tracer and 2.5 ml of the desorbent material methyl acetate. The operations taking place for each test were as follows. The desorbent material was run continuously at a nominal liquid hourly space velocity (LHSV) of 1.0. At some convenient time interval, a pulse of the feed mixture was introduced. The desorbent stream was then resumed at 1 LHSV and continued to pass into the adsorbent column until all of the feed components had been eluted from the column as determined by chromatographic analysis of the effluent material leaving the adsorption column.

Figure 1:
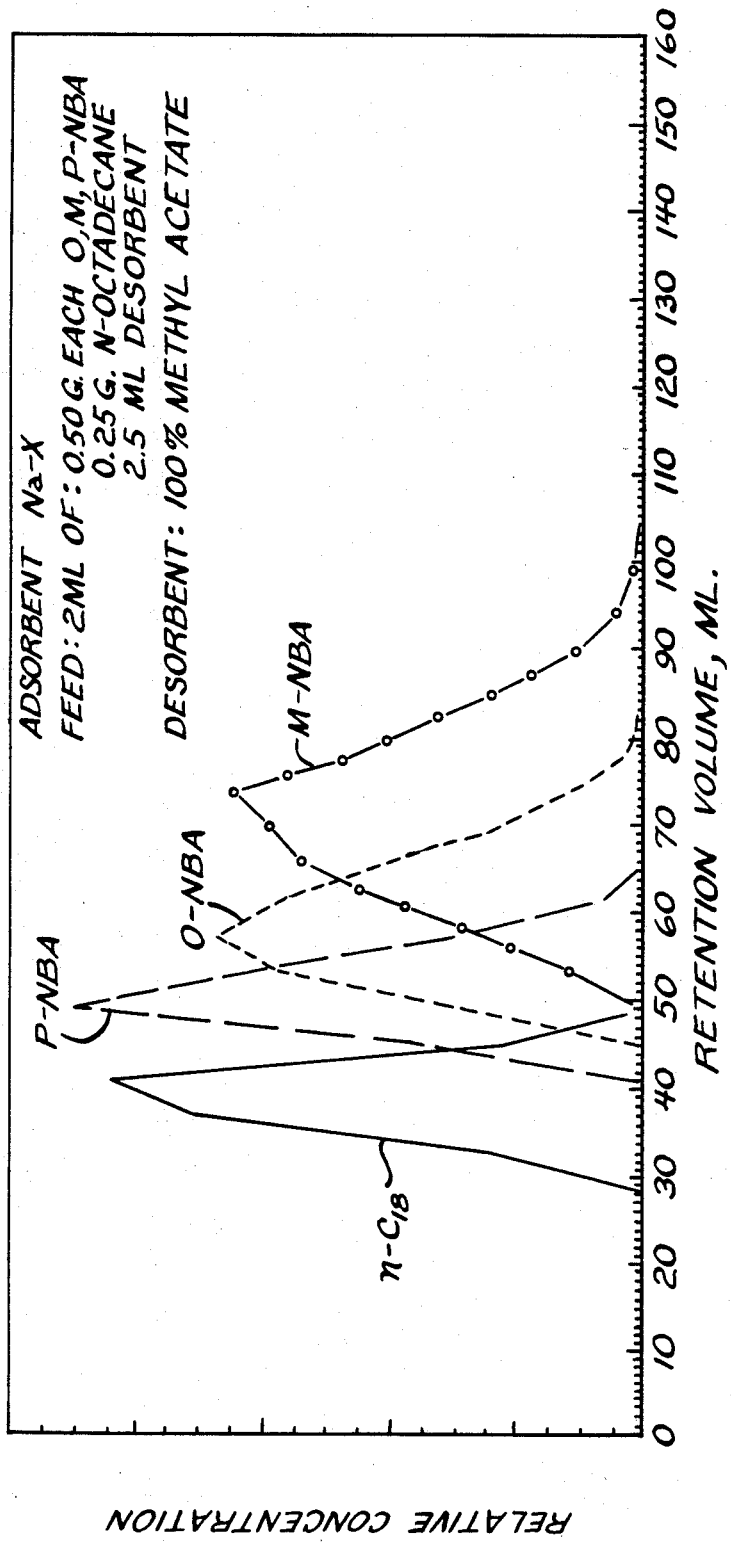
FIGS. 1–13 are chromatographic traces of the pulse tests described in Examples I through IV, illustrating the separations achieved with various zeolites and desorbents.

The results of the test of this Example are shown on the accompanying FIG. 1 which comprises the chromatographic trace. Retention volumes and selectivities derived from the traces are as follows:

| Selectivity | Retention Volumes ml |
|---|---|
| $(B)_{m/o} = 1.65$ | META: 70.6 |
| $B_{m/p} = 2.76$ | ORTHO: 58.2 |
| $B_{o/p} = 1.68$ | PARA: 50.5 |

It is clear from the test that the separation of meta-nitrobenzaldehyde from the other isomers is readily achieved by the process of the present invention. There is minimal overlap between the meta-curve and curves for the ortho- and para-isomers. Selectivities for the meta-isomer relative to the ortho- and para-isomers are sufficiently high for good separation.

EXAMPLE II

The test of Example I was repeated for several additional X-type molecular sieves. In a first test a type X sodium-exchanged zeolite and in a second test, a lithium-exchanged type X zeolite was used.

Figure 2:
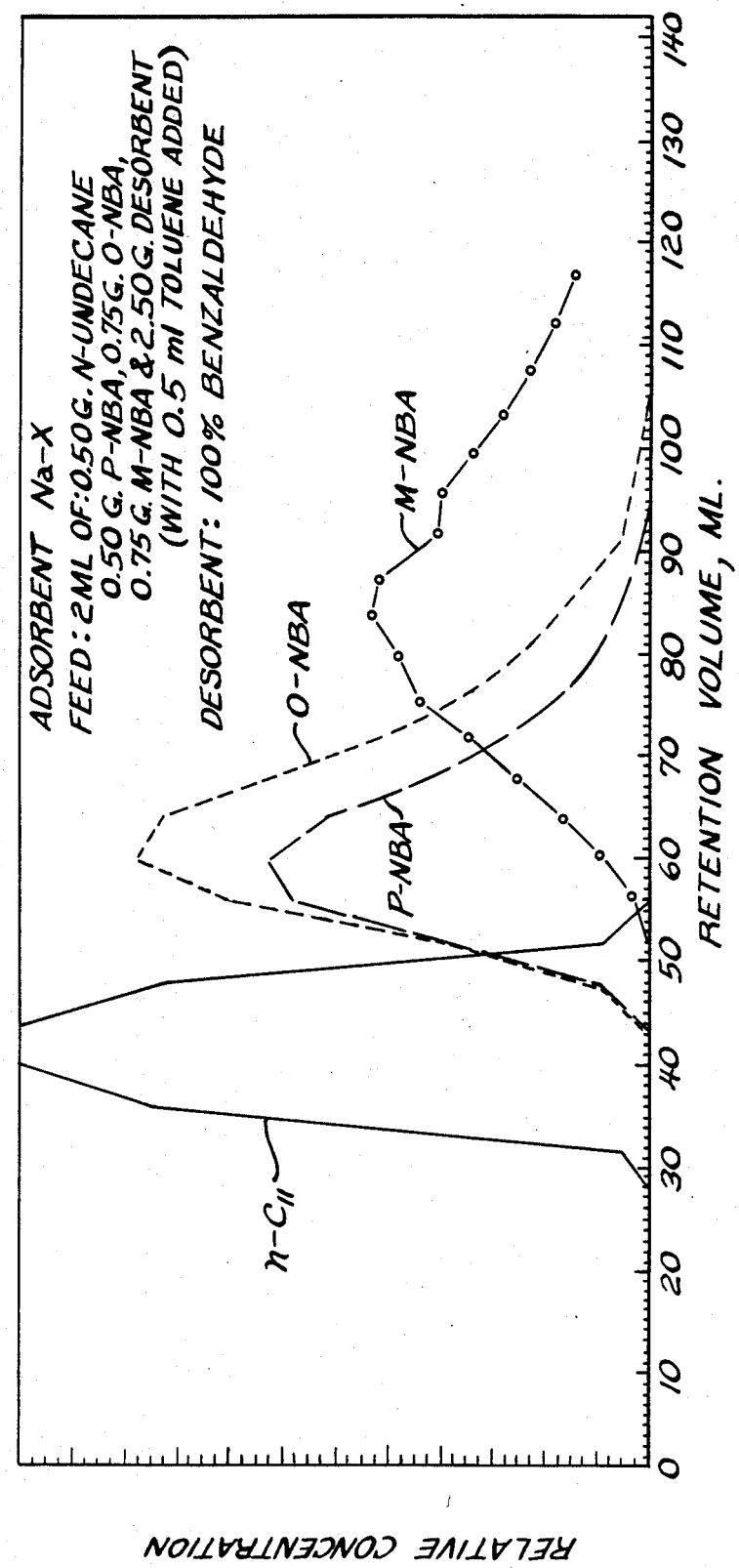
Figure 3:
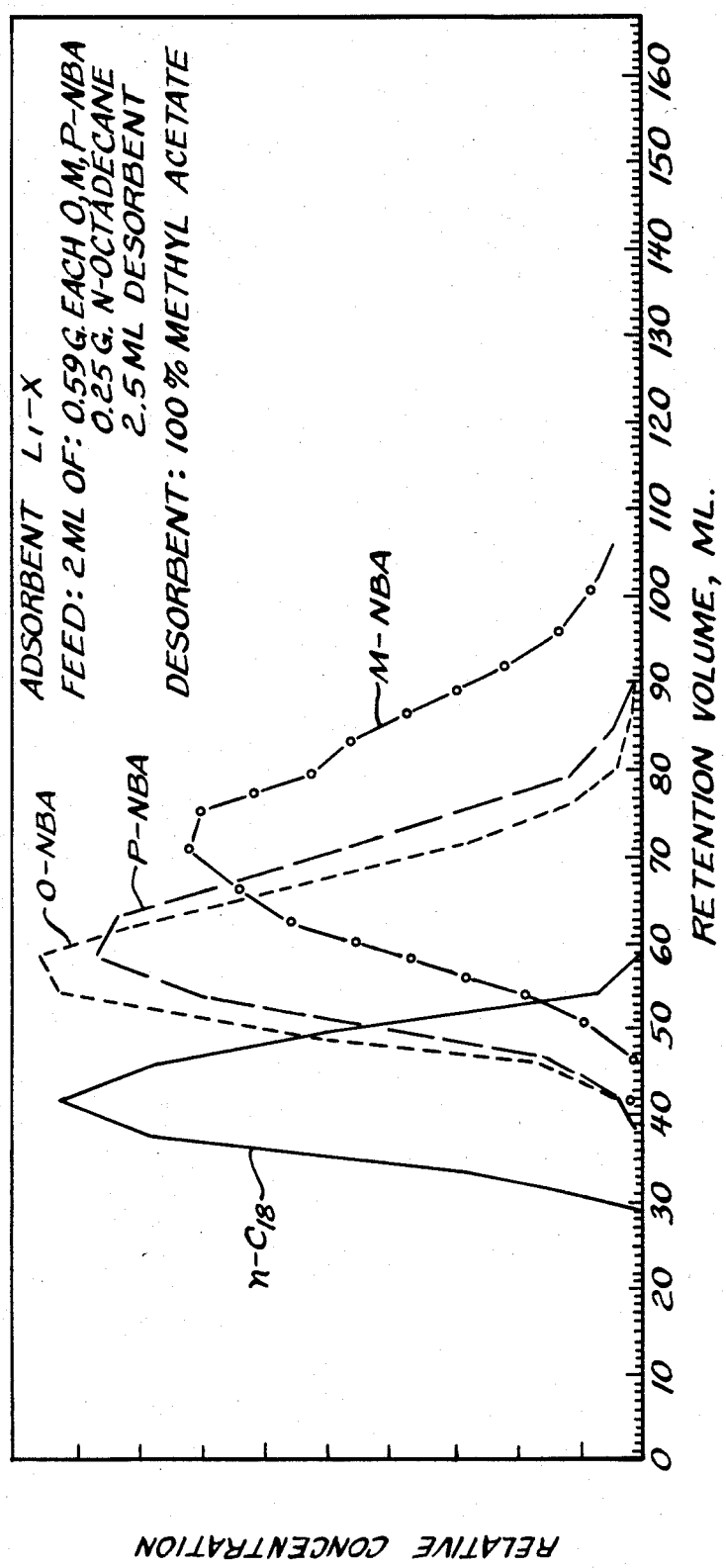
Figure 4:
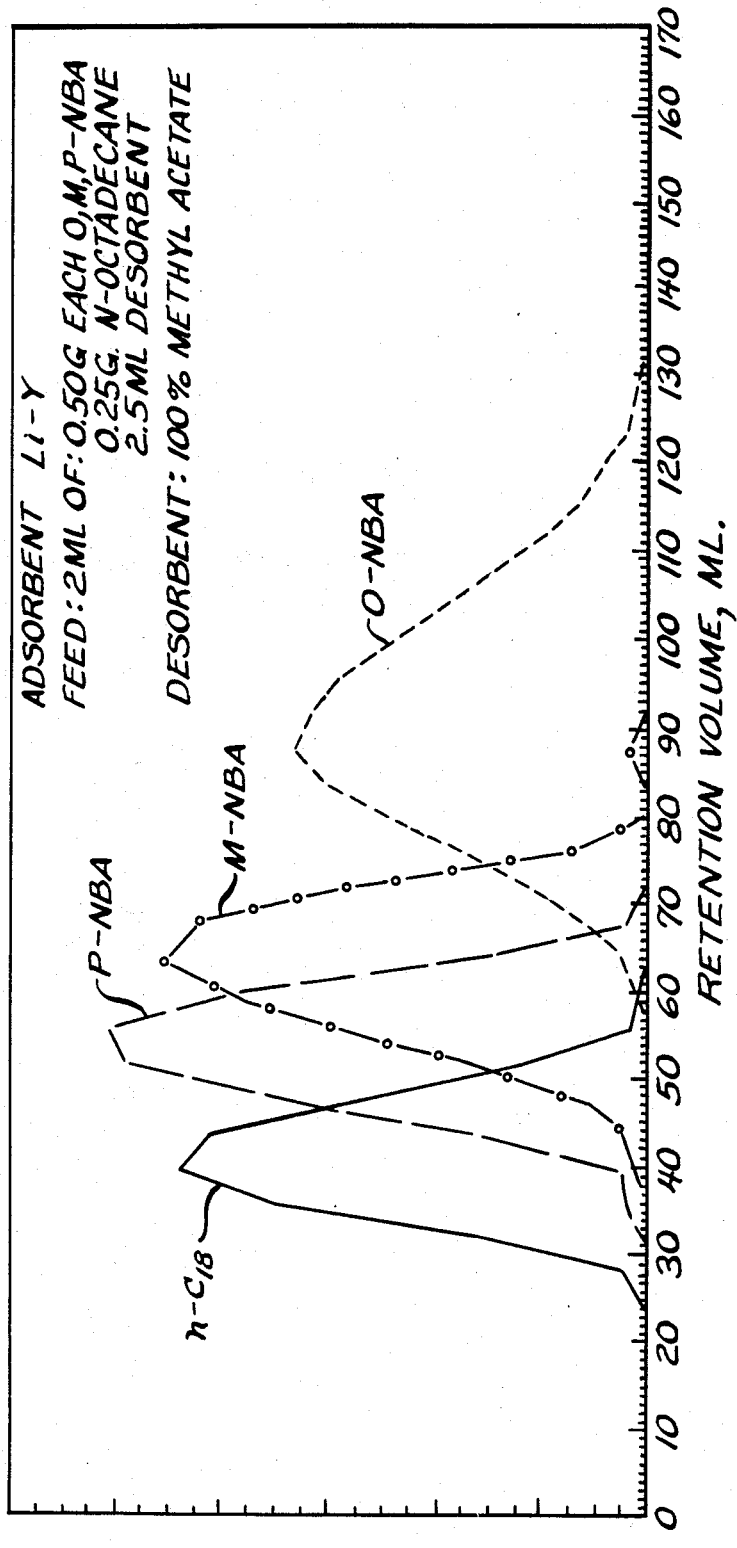
Figure 5:
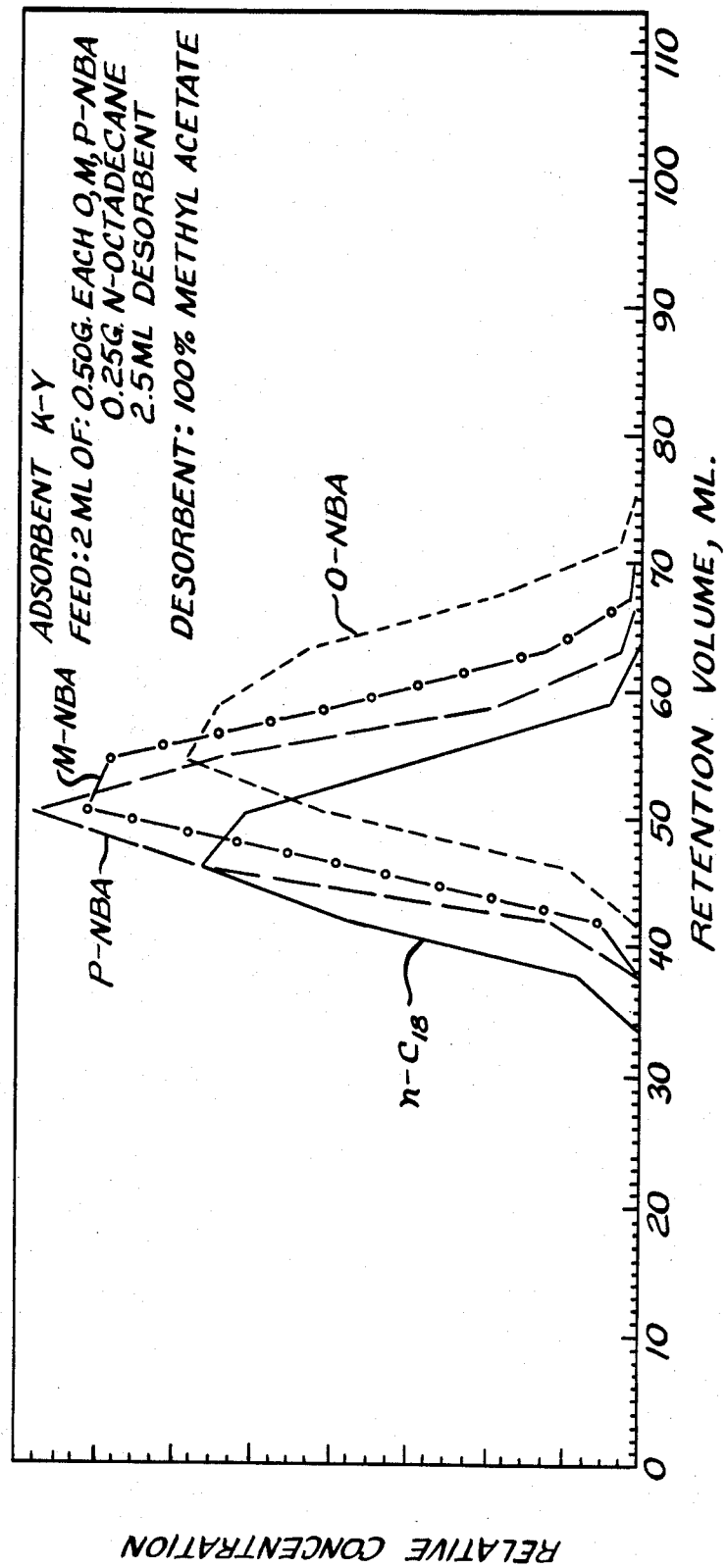
Figure 6:
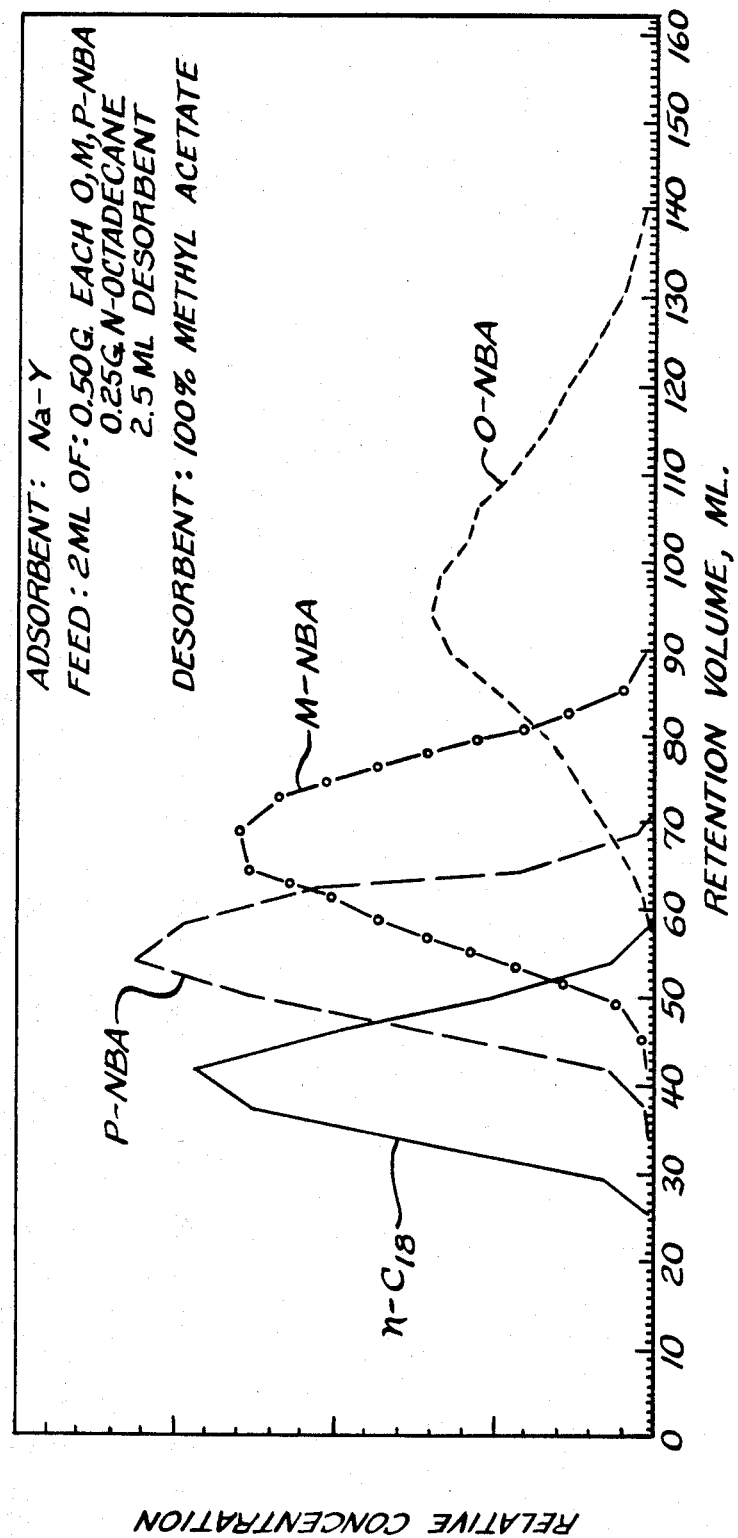
Figure 7:
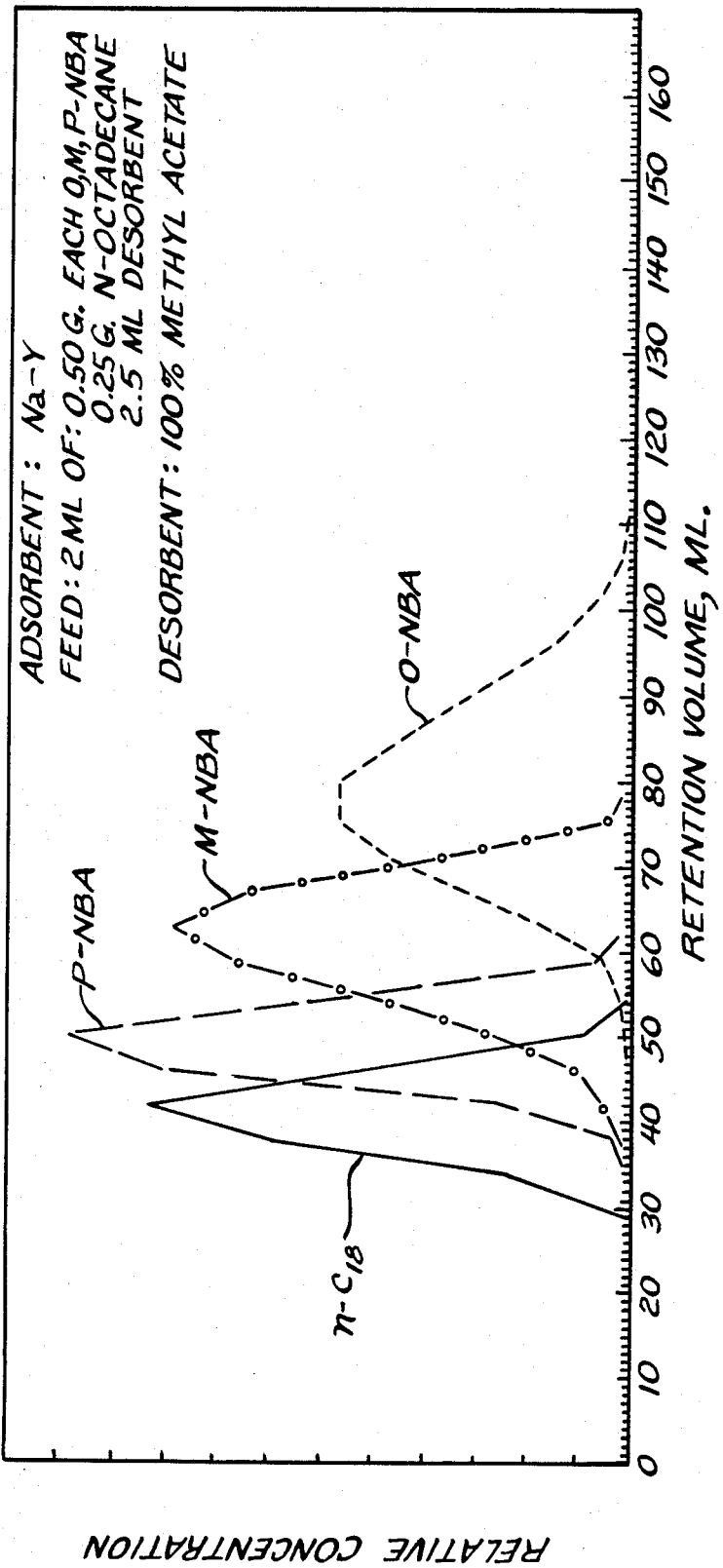
Figure 8:
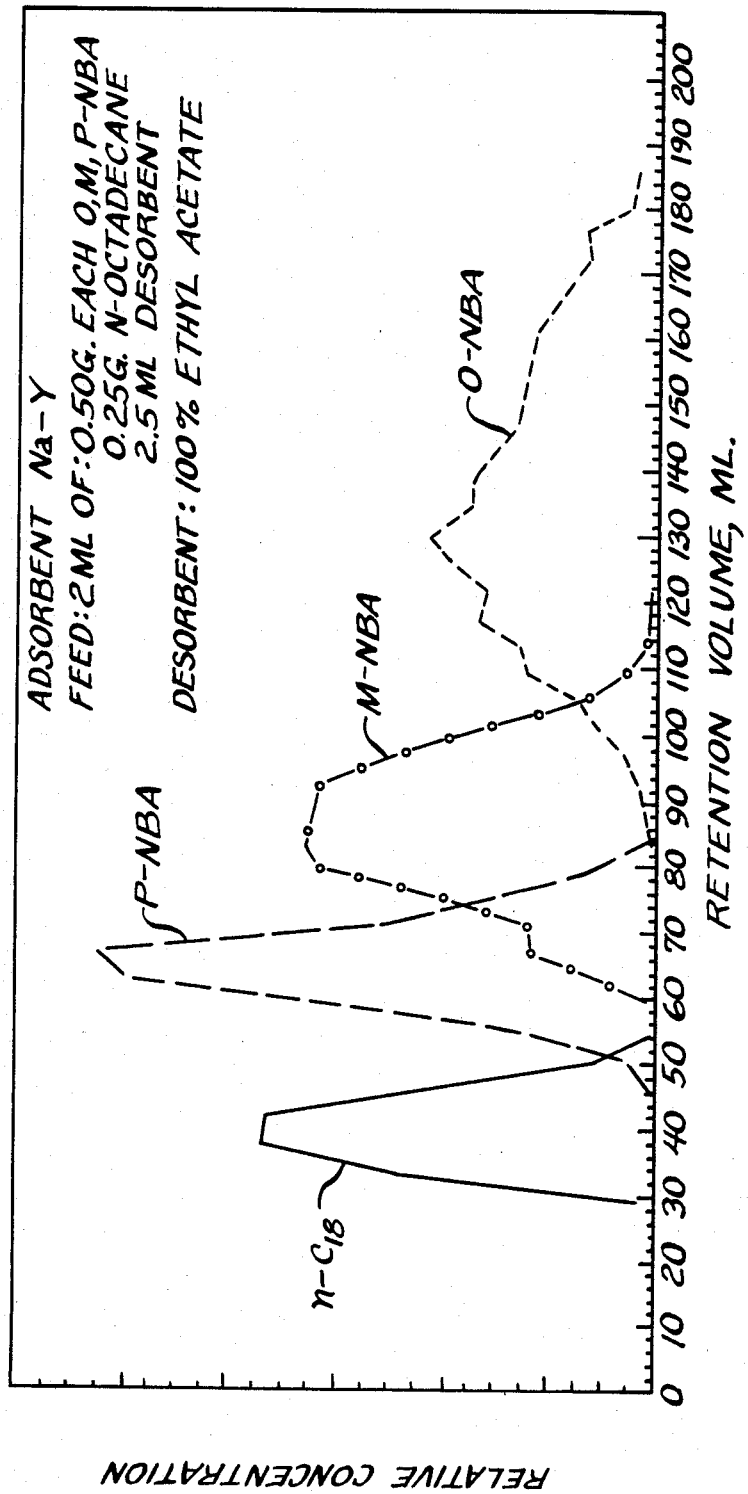
Figure 9:
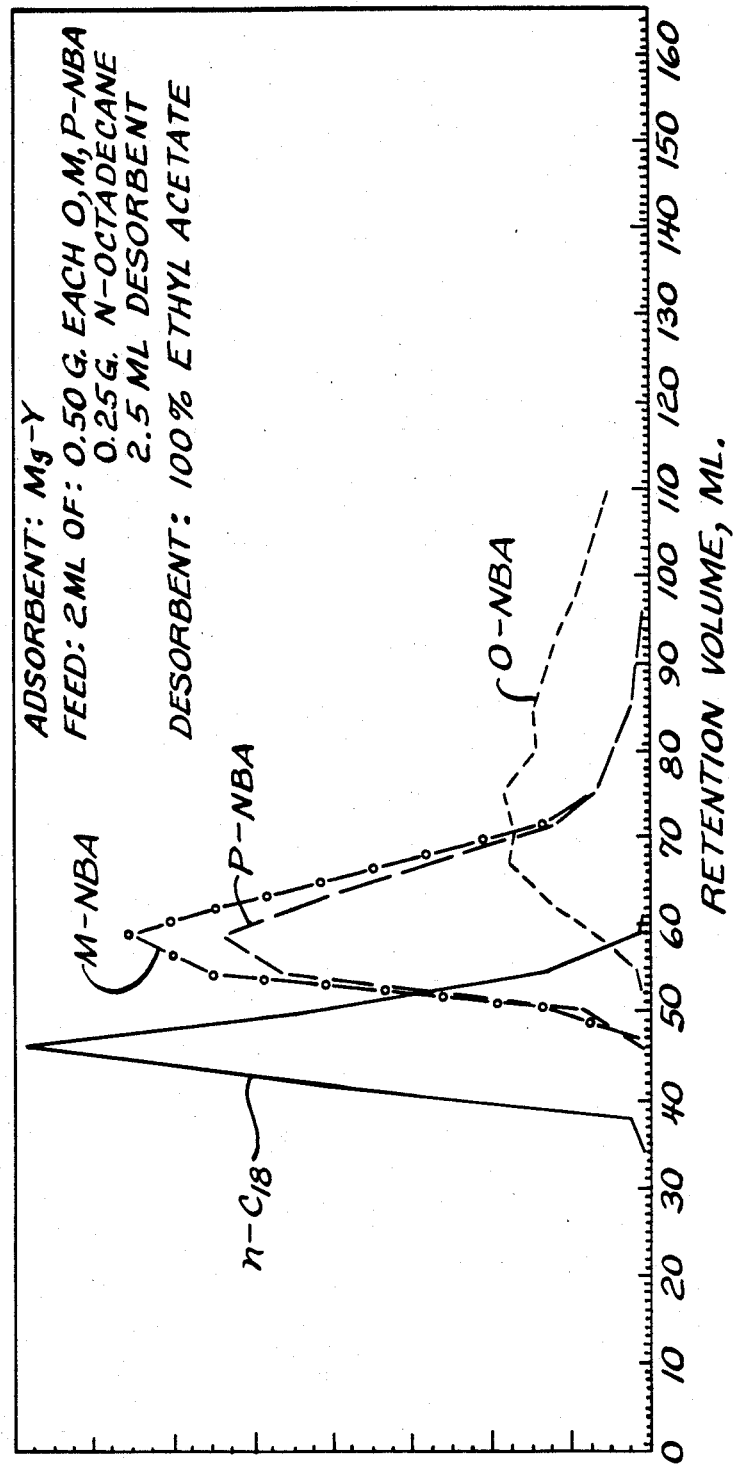
Figure 10:
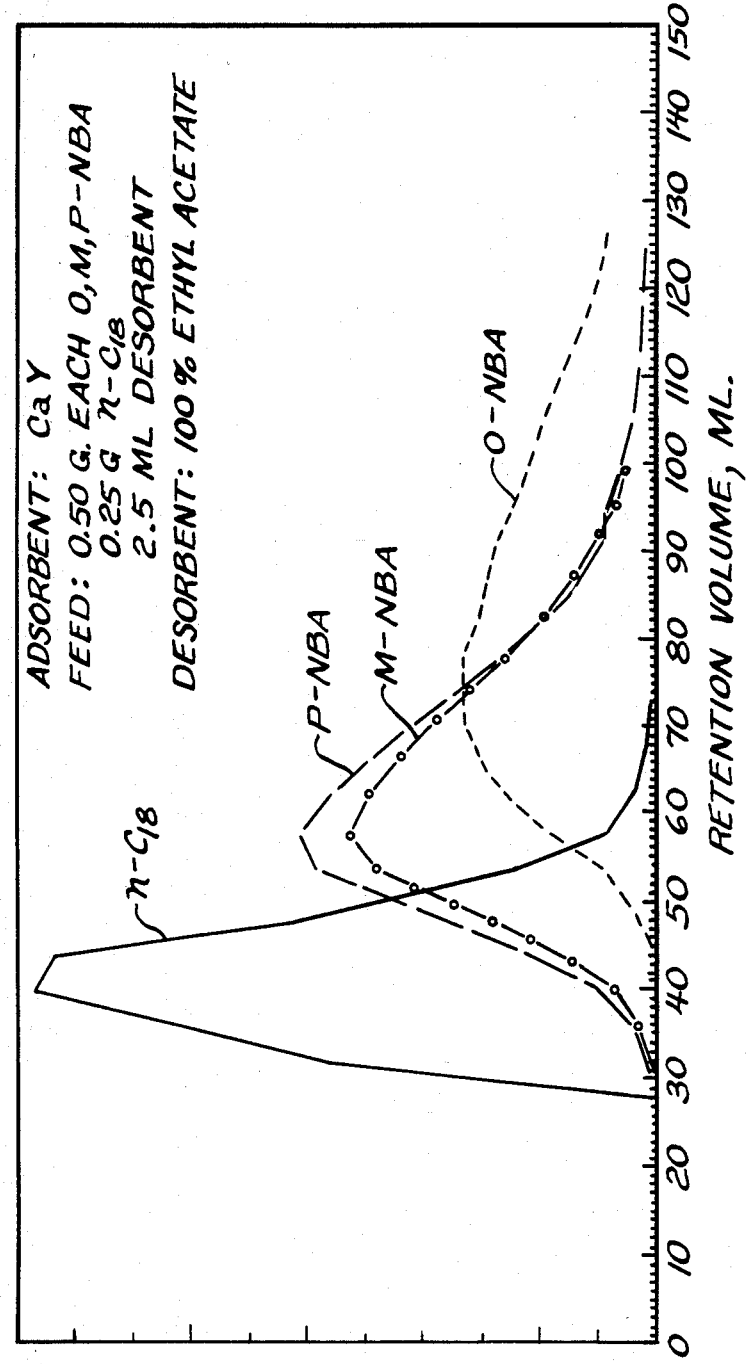
Figure 11:
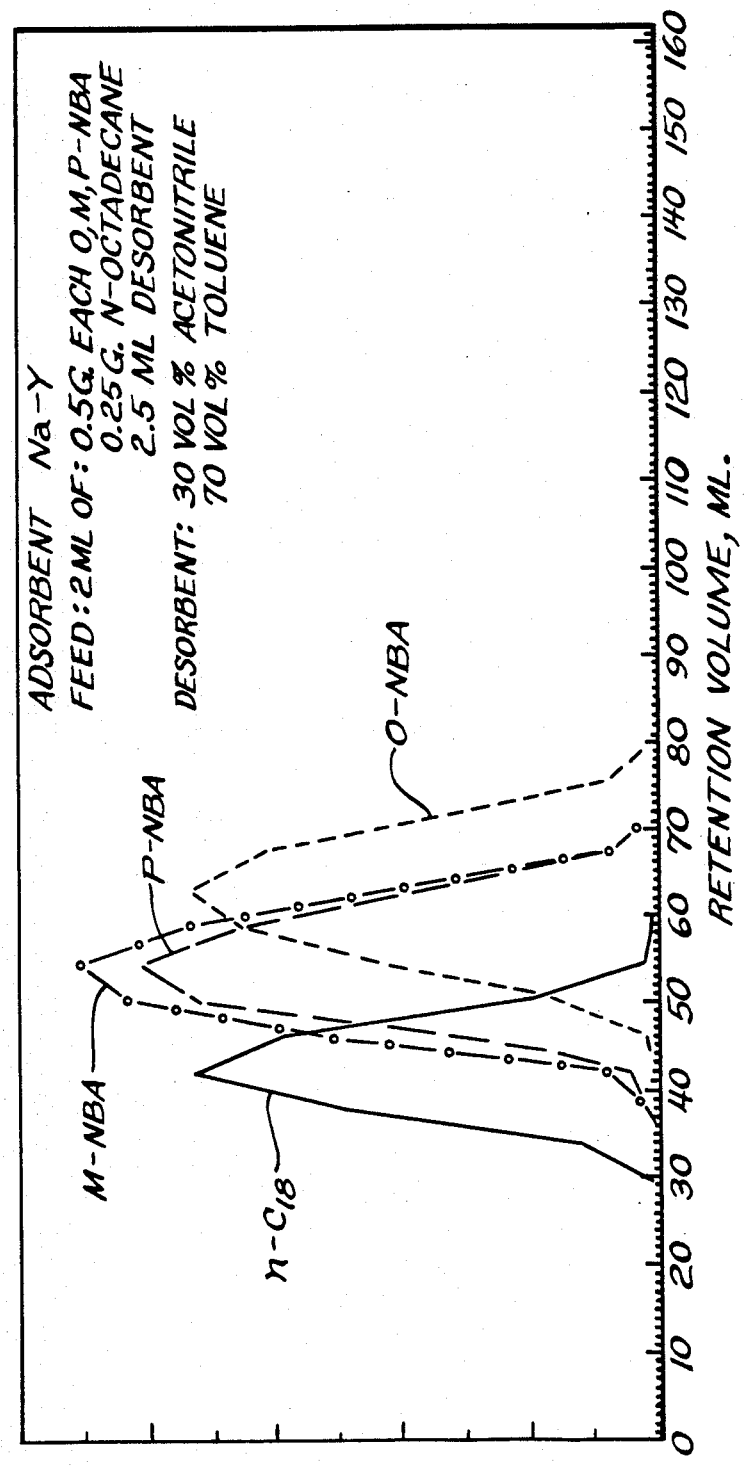
Figure 12:
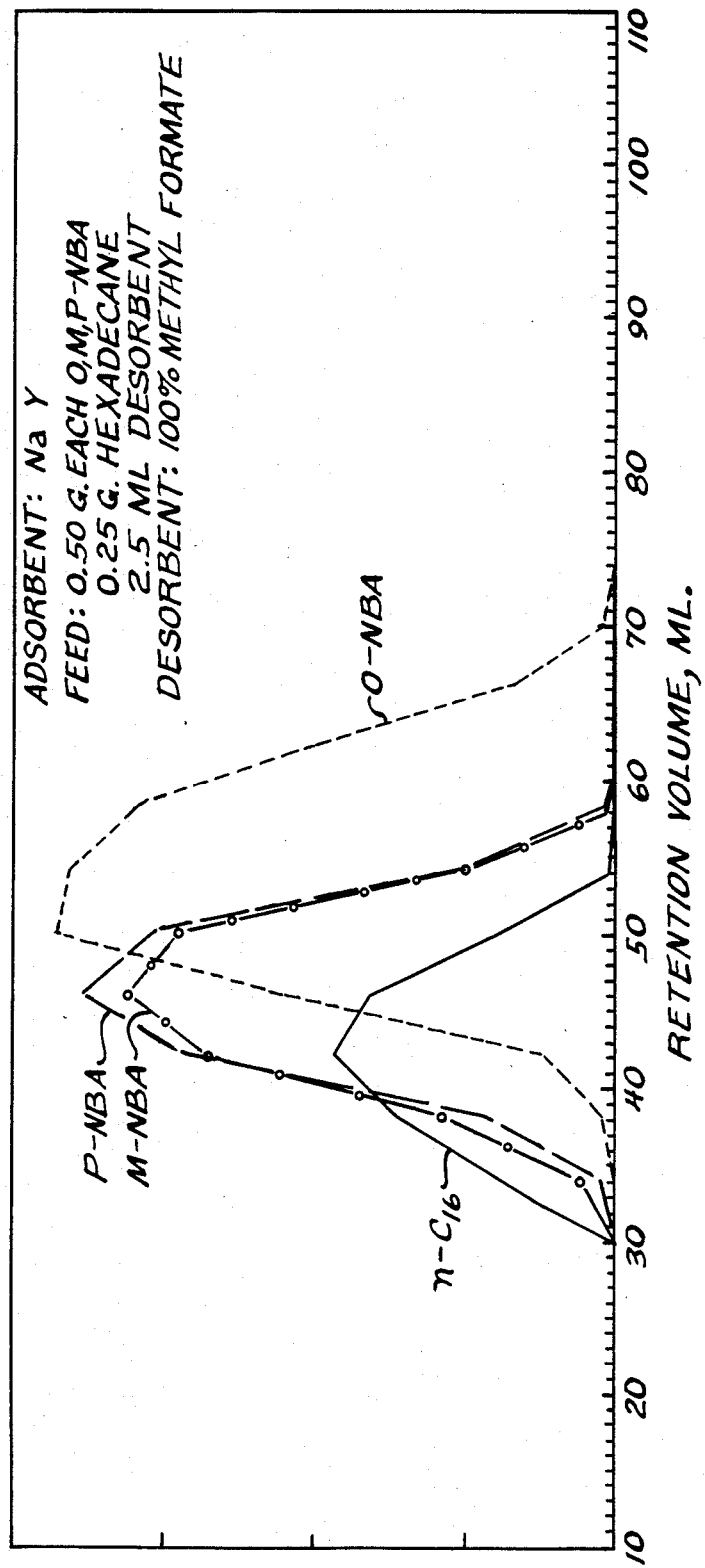

The results of the above two tests are shown on the accompanying FIGS. 2 and 3. The selectivities are as follows:

TABLE

| FIG. No. | Adsorbent | Desorbent | Selectivity |
|---|---|---|---|
| 2 | NaX | Benzaldehyde | $B_{m/o} = 2.17$ |
|   |   |   | $B_{o/p} = 1.12$ |
|   |   |   | $B_{m/p} = 2.42$ |
| 3 | LiX | Methyl acetate | $B_{m/o} = 1.88$ |
|   |   |   | $B_{m/p} = 1.58$ |
|   |   |   | $B_{p/o} = 1.19$ |

It is clear form FIGS. 2 and 3 and the data in the above table that the adsorbent of the present invention exhibits acceptable selectivity for meta-nitrobenzaldehyde.

EXAMPLE III

The pulse test was repeated for another group of zeolites each of which shows a preferential adsorption of the ortho-isomer. Except as noted in the following table, the conditions were the same as Example 1.

| FIG. No. | Adsorbent | Desorbent | Selectivities $B_{o/m}$ | $B_{o/p}$ | $B_{m/p}$ | Other Comment |
|---|---|---|---|---|---|---|
| 4 | LiY | Methyl Acetate | 2.25 | 3.88 | 1.73 | |
| 5 | KY | Methyl Acetate | 1.90 | 3.23 | 1.70 | |
| 6 | NaY | Methyl Acetate | 2.17 | 3.99 | 1.84 | $SiO_2/Al_2O_3 = 5$ |
| 7 | NaY | Methyl Acetate | 1.80 | 4.60 | 2.55 | $SiO_2/Al_2O_3 = 3.07$ |
| 8 | NaY | Ethyl Acetate | 2.01 | 3.83 | 1.90 | |
| 9 | MgY | Ethyl Acetate | 2.47 | 2.47 | 1.00 | |
| 10 | CaY | Ethyl Acetate | 1.96 | 2.15 | 1.10 | temp = 104° C. |
| 11 | NaY | 30% (vol.) acetonitrile 70% (vol.) Toluene | 1.75 | 1.62 | 1.08 | |
| 12 | NaY | Methyl Formate | 1.97 | 1.97 | 1.0 | temp = 80° C. |

EXAMPLE IV

Figure 13:
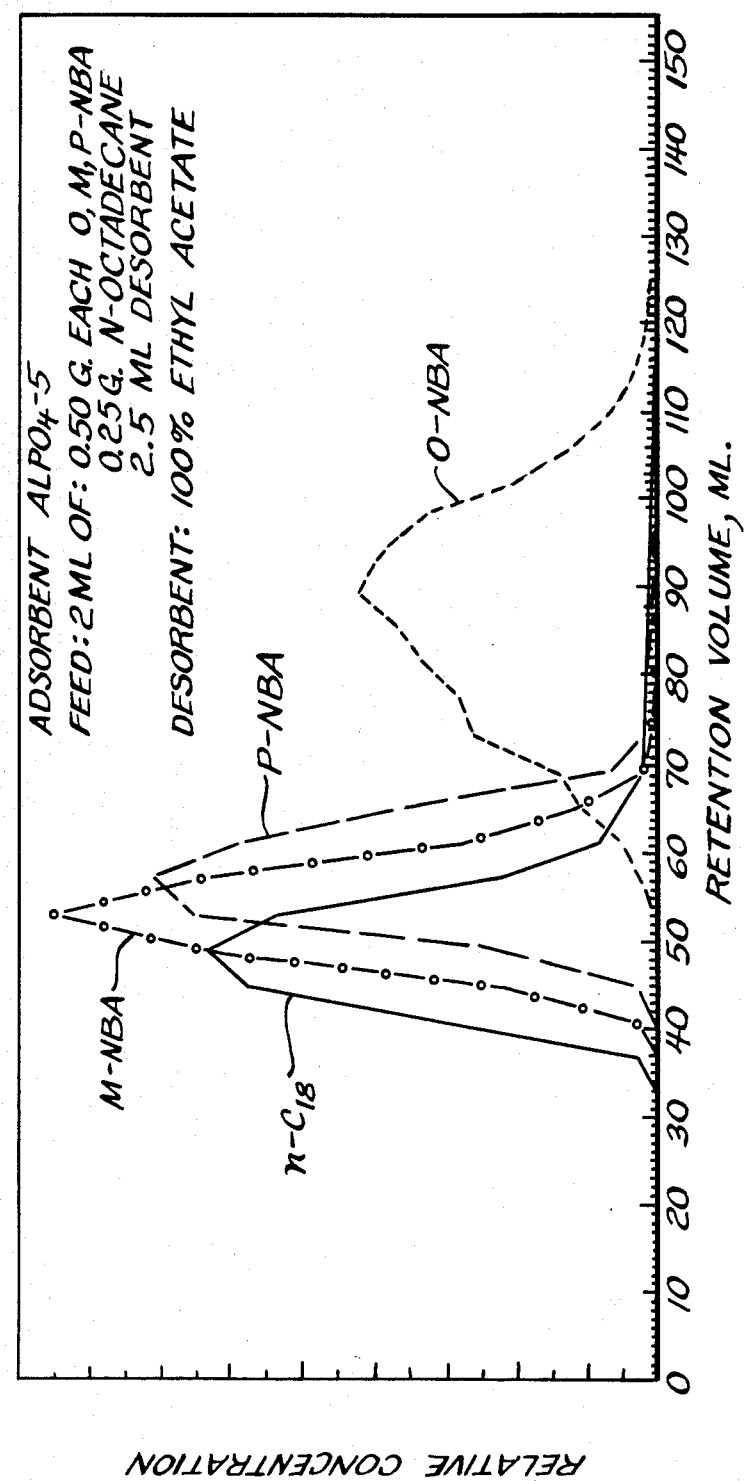

AlPO$_4$–5, which can be prepared according to the procedure set forth in Wilson et al. U.S. Pat. No. 4,310,440 Examples 1–26, having 8 Å pores, was mixed with a clay binder to produce an adsorbent of 20–60 mesh particle size. The pulse test column was filled with the adsorbent and a 2 cc pulse of feed material containing 0.50 g each of o-nitrobenzaldehyde, m-nitrobenzaldehyde and p-benzaldehyde, 0.25 g n-octadecane and 2.5 ml desorbent was injected into the column as previously explained. Following the feed, the flow of ethyl acetate desorbent was continued. Ortho-nitrobenzaldehyde was preferentially adsorbed and was well-separated from the meta- and para-isomers as shown in FIG. 13. The selectivities (B) were as follows:

$B_{o/m} = 6.75$
$B_{m/p} = 4.23$
$B_{p/m} = 1.60$

We claim as our invention:

1. A process for separating the isomers of nitrobenzaldehyde from a feed mixture comprising at least two isomers of nitrobenzaldehyde, which comprises contacting said mixture at adsorption conditions with an adsorbent comprising an X-type zeolite having sodium or lithium cations at exchangeable cationic sites, a Y-type zeolite having sodium, lithium, potassium, magnesium or calcium cations at the cation exchangeable sites, or a crystalline aluminum phosphate zeolite, selectively adsorbing one of said isomers to the substantial exclusion of the other isomers, and recovering a high purity nitrobenzaldehyde as a raffinate stream.

2. The process of claim 1 wherein said feed mixture contains ortho-, meta- and para-nitrobenzaldehyde.

3. The process of claim 1 wherein said one isomer is removed from said adsorbent by contacting said adsorbent with a liquid desorbent material selected from the group consisting of methyl acetate, methyl formate, benzaldehyde, ethyl acetate and acetonitrile at desorption conditions to remove said one isomer as an extract stream.

4. The process of claim 3 wherein said adsorbent is a Y-type zeolite, and said adsorbed isomer is ortho-nitrobenzaldehyde.

5. The process of claim 3 wherein said adsorbent is an X-type zeolite and said adsorbed isomer is meta-nitrobenzaldehyde.

6. The process of claim 3 wherein said adsorption and desorption conditions comprise a temperature from about 20° C to about 250° C.

7. The process of claim 1 wherein said process is effected with a simulated moving bed flow system.

8. The process of claim 7 wherein said simulated moving bed flow system is of the countercurrent type.

9. The process of claim 7 wherein said simulated moving bed flow system is of the cocurrent high efficiency type.

10. A process for separating ortho-nitrobenzaldehyde from a feed mixture comprising ortho-nitrobenzaldehyde and at least one other isomer of nitrobenzaldehyde, which comprises contacting said mixture at adsorption conditions with an adsorbent comprising a type Y-zeolite having potassium, sodium, lithium, magnesium or calcium cations at exchangeable cationic sites or a crystalline aluminum phosphate zeolite, selectively adsorbing said ortho-isomer to the substantial exclusion of the remaining isomers, removing said remaining isomers from contact with adsorbent, and thereafter recovering high purity ortho-nitrobenzaldehyde.

11. The process of claim 10 wherein said feed mixture contains ortho-, meta- and para-nitrobenzaldehyde.

12. The process of claim 10 wherein said ortho-nitrobenzaldehyde is recovered by contacting said absorbent with a liquid material selected from the group consisting of methyl acetate, ethyl acetate, methyl formate and acetonitrile at desorption conditions to remove said ortho-isomer as an extract steam.

13. The process of claim 12 wherein said adsorption and desorption conditions comprise a temperature from about 20° C. to about 250° C.

14. The process of claim 10 wherein said process is effected with a simulated moving bed flow system.

15. The process of claim 14 wherein said simulated moving bed flow system is of the countercurrent type.

16. The process of claim 14 wherein said simulated moving bed flow system is of the cocurrent high efficiency type.

17. A process for separating meta-nitorbenzaldehyde from a feed comprising meta-nitrobenzaldehyde and at least one other isomer of nitrobenzaldehyde which comprises contacting said mixture at adsorption conditions with an adsorbent comprising a type X-zeolite having sodium or lithium cations at exchangeable cationic sites, selectively adsorbing said meta-isomer to the substantial exclusion of the remaining isomers, removing said remaining isomer from contact with said adsorbent, and thereafter recovering high purity meta-nitrobenzaldehyde.

18. The process of claim 17 wherein said feed mixture contains ortho-, meta- and para-nitrobenzaldehyde.

19. The process of claim 17 wherein said meta-nitrobenzaldehyde is recovered by contacting said adsorbent with a liquid material selected from the group consisting of methyl acetate and benzaldehyde at desorbent conditons to remove said meta-isomer as an extract stream.

20. The process of claim 17 wherein said adsorption and desorption conditions comprises a temperature from about 20° C. to about 250° C.

* * * * *

UNITED STATES PATENT AND TRADEMARK OFFICE
CERTIFICATE OF CORRECTION

PATENT NO.  : 4,714,783
DATED       : December 22, 1987
INVENTOR(S) : Hermann A. Zinnen et al It is certified that error appears in the above-indentified patent and that said Letters Patent is hereby corrected as shown below:

At column 12, line 23, delete "raffinate" and insert therefor --extract--.

At column 3, lines 30-40, add lines to connect each of the "$NO_2$" groups to the benzene structure, i.e.:

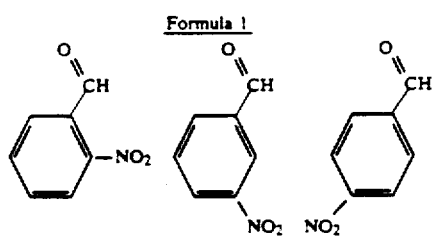

Formula 1

Signed and Sealed this

Third Day of August, 1993

Attest:

MICHAEL K. KIRK

*Attesting Officer*       Acting Commissioner of Patents and Trademarks